United States Patent [19]

Strohmeier et al.

[11] Patent Number: 4,883,409
[45] Date of Patent: Nov. 28, 1989

[54] PUMPING APPARATUS FOR DELIVERING LIQUID AT HIGH PRESSURE

[76] Inventors: Fred Strohmeier, Ringstrasse 58, D-7587 Rheinmunster 2; Klaus Witt, Quellenstrasse 16, D-7538 Keltern 3, both of Fed. Rep. of Germany

[21] Appl. No.: 246,479

[22] Filed: Sep. 19, 1988

[30] Foreign Application Priority Data

Sep. 26, 1987 [EP] European Pat. Off. ........ 87114091.9

[51] Int. Cl.$^4$ ............................................ F04B 41/06
[52] U.S. Cl. ........................................ 417/43; 417/44; 417/212; 417/265; 210/101
[58] Field of Search ...................... 417/43, 18, 265, 44, 417/45, 212; 210/101

[56] References Cited

U.S. PATENT DOCUMENTS

| | | | |
|---|---|---|---|
| 3,291,350 | 12/1966 | Malec | 417/489 |
| 4,089,624 | 5/1978 | Nichols et al. | 417/419 |
| 4,352,636 | 11/1982 | Patterson et al. | 417/42 |
| 4,420,393 | 12/1983 | Smith | 210/101 |
| 4,422,942 | 12/1983 | Allington | 210/101 |
| 4,556,367 | 12/1985 | Schmid | 417/18 |
| 4,595,495 | 6/1986 | Yotam et al. | 210/101 |
| 4,595,496 | 6/1986 | Carson | 210/101 |
| 4,600,365 | 7/1986 | Riggenmann | 417/265 |
| 4,681,513 | 7/1987 | Saito et al. | 417/2 |
| 4,714,545 | 12/1987 | Bente et al. | 210/101 |

FOREIGN PATENT DOCUMENTS 2347717  3/1974  Fed. Rep. of Germany ...... 417/419

Primary Examiner—Carlton P. Croyle
Assistant Examiner—D. Scheuermann
Attorney, Agent, or Firm—Richard F. Schuette

[57] ABSTRACT

A pumping apparatus for delivering liquid at a high pressure, in particular for use in liquid chromatography, comprises two pistons (10, 20) which reciprocate in pump chambers (7,18), respectively. The output of the first pump chamber (7) is connected via a valve (13) to the input of the second pump chamber (18). The pistons are driven by linear drives (30,31), e.g., ball-screw spindles. The stroke volume displaced by the piston (10) is freely adjustable by corresponding control of the angle by which the shaft of the drive motor (36) is rotated during a stroke cycle. The control circuitry is operative to reduce the stroke volume when the flow rate which can be selected by user at the user interface (42) is reduced, thus leading to reduced pulsations in the outflow of the pumping apparatus. The pumping apparatus can also be used for generating solvent gradients when a mixing valve (2) connected to different solvent containers (A,B,C,D) is coupled to the input of the pumping apparatus (FIG. 1).

12 Claims, 6 Drawing Sheets

PUMPING APPARATUS FOR DELIVERING LIQUID AT HIGH PRESSURE

The invention relates to a pumping apparatus for delivering liquid at a high pressure, in particular a pumping apparatus for solvent delivery in liquid chromatography. Such a pumping apparatus is used, e.g., in liquid chromatography to pump the mobile phase (solvents or mixtures of solvents) through the chromatographic system including the separation column. The pumping apparatus forms a part of the solvent delivery system which may comprise additional units for drawing in and for mixing solvents.

In the chromatographic analysis, it is desirable that the flow rate of the liquid delivered to the column is adjustable over a wide range of flow rates. It is furthermore desirable that the solvent delivery system permits the generation of mixtures of solvents and to change the mixing ratio of the various solvents of the mixture in the course of time (gradient operation). Such versatility of the solvent delivery system permits to optimize the analysis conditions for the specific sample to be chromatographically separated.

Although the flow rate should be adjustable, it is very important that a once adjusted flow rate is kept as constant as possible. If the flow rate through the separation column would fluctuate, variations in the retention time of the examined sample would occur so that the areas of the chromatographic peaks produced by a detector connected to the outlet of the column, e.g., an absorption detector, a fluorescence detector, or a refractive index detector, would vary. Since the peak areas are representative for the concentration of the chromatographically separated sample substances, fluctuations in the flow rate would impair the accuracy and the reproducibility of quantitative measurements.

Some pumping systems like reciprocating pumps with a single piston have inherent flow variations because the piston delivers only during a portion of a pump cycle. To reduce such pump pulsations, it is known to use a dual piston pump having two interconnected pump heads each with a reciprocating piston. The pistons are driven via cams and a cam-shaft with a predetermined phase difference so that the resulting outflow is comparatively smooth. Such a dual piston pump driven via cams and a common cam shaft is known from U.S. Pat. No. 4,352,636.

At the high pressure encountered in high performance liquid chromatography, compressiblility of the solvents becomes noticable resulting in an additional source for flow pulsations. The reason is that during each compression cycle of the pump, the first piston has to move a certain path to compress the liquid to its final delivery pressure before actual delivery of liquid starts. As a consequence thereof, pulsations in the outflow occur at the pump frequency. These flow pulsations are particularly disturbing at low flow rates. The reason is that the percent magnitude of pulsations remains substantially constant over a wide range of flow rates but that the amplitudes of the peaks in the chromatogram become smaller when the flow rate is reduced, in particular when smaller separation columns are used, so that the influence of the flow pulsations on the chromatographic results is more pronounced at lower flow rates.

From the above-mentioned patent U.S. Pat. No. 4,352,636, it is known to reduce the pulsations caused by the compressibility of the liquids by using specially designed cams which are contoured such as to produce the same amount of outflow of pressurized liquid at all points in the cycle of rotation of the cam shaft except for a short interval at the beginning of the expulsion stroke of the first piston. The thus produced precompression phase and the resulting positive outflow pulse is to compensate for compressibility of the liquid. The precompression phase is dependent on a variety of parameters like volume at the top dead centre of the first piston, stroke volume, pressure in the pump, compressibility of the liquid, stiffness of the pumping system, closing performance of the valves. Since not all of these parameters can be precisely determined, a remaining pulsation in the outflow of the pump is to be expected. Furthermore, the known pumping apparatus has a comparatively complex mechanical design requiring precisely machined cams.

Relative to this prior art, it is an object of the invention to provide a pumping apparatus for delivering liquid at high pressure according to the preamble of claim 1 which has a simpler mechanical design and which substantially avoids over a wide range of flow rates the problems caused by interferences of pulsations of the flow of the delivered liquid with the chromatographic measuring results.

According to claim 1, this object is solved for an apparatus as in the preamble in that control means are provided which are coupled to the drive means reciprocating the pistons, the control means being operative to adjust the stroke lengths of the pistons between their top dead centre and their bottom dead centre, respectively, permitting an adjustment of the amounts of liquid displaced by the first and second piston, respectively, during a pump cycle such that pulsations in the flow of the liquid delivered to the output of the pumping apparatus are reduced.

In order to see how the provision of an adjustable stroke volume leads to a reduction in the flow pulsations, the following is to be considered:

In known solvent delivery systems, the flow rate is changed by changing the frequency of reciprocation of the pistons so that the pistons move at a higher frequency when a higher flow rate is selected, whereas the stroke volume remains the same when the flow rate is altered. According to the present invention, however, the flow rate is changed by changing both the frequency of reciprocation of the pistons and the stroke volume. In a preferred embodiment of the invention, the stroke volume is decreased with the flow rate. Thus, when the stroke volume becomes smaller, the volume which has to be compressed to the final pressure before delivery starts also becomes smaller. Since the volume to be compressed is smaller, the compression phase becomes shorter resulting in smaller pulsations of the outflow of the pump.

It is a further consequence of the variation of the stroke volume as a function of the flow rate that, particularly at low flow rates, the frequency of reciprocation of the pistons is higher than in a prior art pump having a fixed stroke for all flow rates. This increase in the frequency of reciprocation leads to a corresponding increase in the frequency of any remaining pulsations of the pump output which has advantageous effects on the reproducibility of quantitative chromatographic measurements. In contrast to low frequency pulsations which may affect the retention times and areas of different peaks in the chromatogram in different ways, high frequency pulsations are more like a uniform background signal which affects the whole chromatogram in substantially the same manner. The increase of the frequency of the pulsations is particularly advantageous when a detector is used which is very sensitive to flow pulsations, e.g., a refractive index detector.

The pumping apparatus according to the invention can not only be used in an isocratic solvent delivery system wherein the input of the pumping apparatus is permanently connected to only one solvent container such that only one type of solvent can be used in the chromatographic analysis, but also in applications wherein mixtures of solvents have to be produced, for example in gradient operation. For such applications, a known per-se mixing valve having a plurality of inputs coupled to different solvent containers can be connected with its output to the input of the pumping apparatus. The mixing valve is controlled such as to establish selectable connections to a solvent container, respectively, in order to produce the desired solvent mixture so that the selected solvent is drawn in when the first piston is retracted. Since the stroke volume is reduced at small flow rates, the amounts of liquid drawn in during each intake stroke for producing a specific mixing ratio are smaller than in conventional pumps. Due to the smaller packages of liquid drawn in, the pump according to the invention ensures a better mixing of the different solvents sucked in than known pumps. Consequently, an additional mixing chamber as it is used in prior art solvent delivery systems between the output of the pumping apparatus and the input of the separation column is either unnecessary or, at least, a much smaller mixing chamber can be employed so that the unwanted dead volume introduced by such a chamber is substantially reduced. Furthermore, faster gradient changes become possible.

According to the invention, the driving of the pistons can be accomplished by using any drive means which permits the adjustment of the stroke lengths of the pistons. According to a preferred embodiment of the invention, the pistons are coupled to ball-screw drives which translate the rotary motion of the spindles into a linear motion of the pistons. In that way, the stroke volumes can easily be changed by changing the angle through which the spindles are rotated during a pump cycle. Furthermore, a ball-screw drive permits to select any desired displacement/time function for the motion of the pistons during a pump cycle, for example a linear variation of the piston displacement as a function of time or a motion with a pre-compression phase during which a piston is accelerated for a short time. This flexibility is an advantage over prior art pumps which would require a new set of specially designed cams for each new displacement/time function for the piston motion.

The ball-screw drives may either be coupled via gears to a common drive motor, or each ball-screw drive may be coupled to a different drive motor so that an independent operation of the two pistons is permitted. If two separate drive motors are used, it is possible to precompress the aspirated solvent with the first piston before the second piston has finished its delivery stroke.

The transmission of the driving force to each piston can advantageously be accomplished via a ball which can move freely in a recess of an actuating element coupled to the rest of the drive means, e.g. a ball-screw-drive, with the ball contacting a piston holder to which the piston is fixed. Since there is no rigid connection between the drive means and the piston, tilt of the piston can be avoided, resulting in an increased lifetime of the seals of the pump chambers.

According to an embodiment of the invention, a damping unit for damping any remaining flow variations in the outflow of the pump is coupled to the output of the second pump chamber.

Subsequently, embodiments of the invention are explained with reference to the drawings.

FIG. 1 schematically shows a solvent delivery system for a liquid chromatograph incorporating the pumping apparatus according to the invention.

Figure 1:
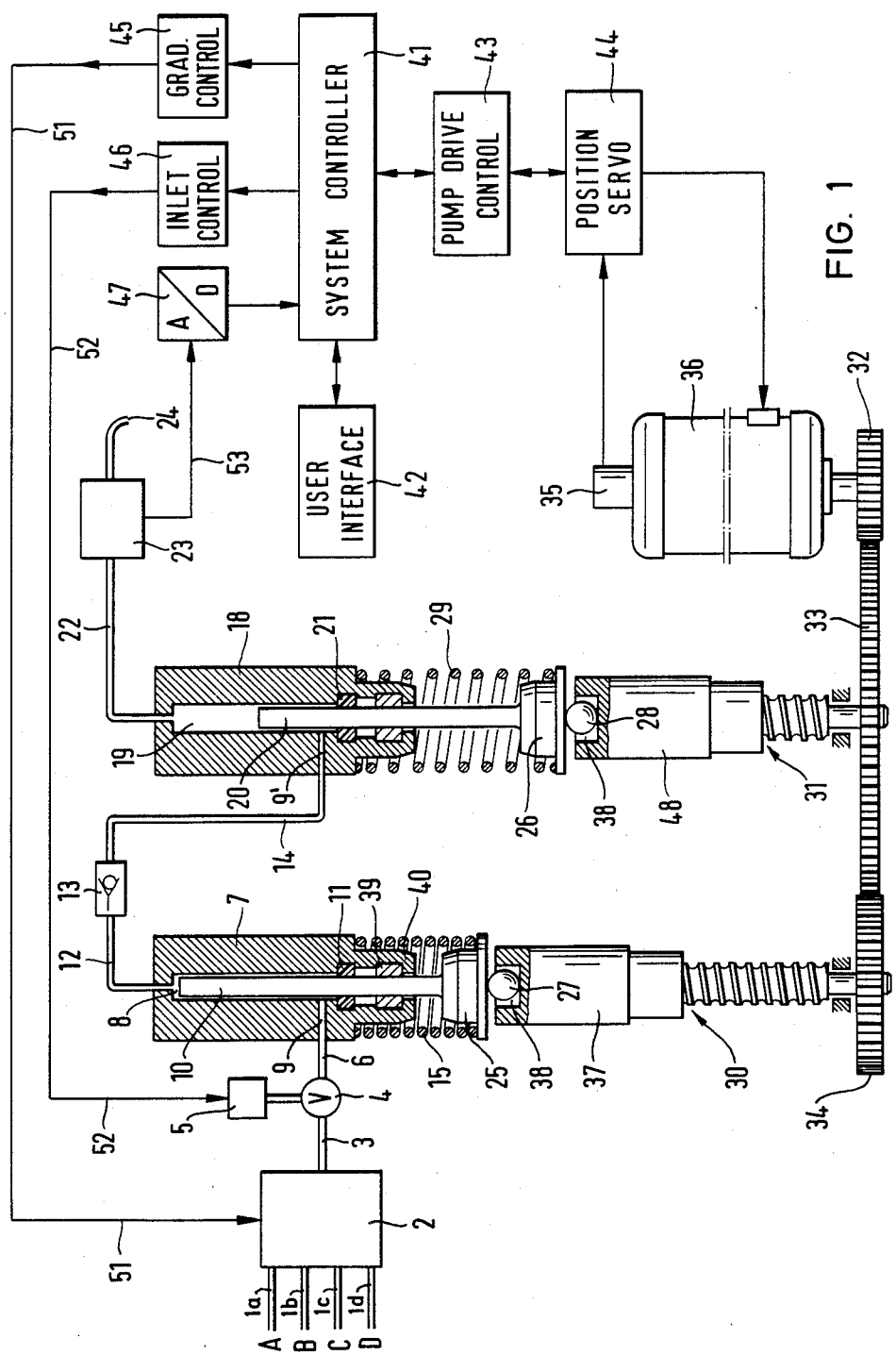
FIG. 1A is an alternate embodiment of the apparatus of FIG. 1.

Referring to FIG. 1, there is shown a solvent delivery system according to the present invention for a liquid chromatograph. Capillary tubes $1a$, $1b$, $1c$, and $1d$ are connected with one end to solvent containers represented by the letters A, B, C, and D, respectively, and with the other end to a mixing valve 2. The mixing valve 2 has an output capillary 3 which is connected to an inlet valve 4 of the first pump chamber. The mixing valve 2 can be operated such that its output capillary 3 is connected to a selected input capillary $1a$, or $1b$, $1c$, or $1d$ to permit flow of a selected solvent to the first pump chamber. By appropriate switching of the mixing valve, a desired solvent composition can be generated. The switching of the mixing valve is accomplished by one or several solenoids (not shown) under the control of a control circuitry which is explained below in more detail. In the embodiment according to FIG. 1, the mixing valve is shown to have four input capillaries, but it is understood that a mixing valve having any number of input capillaries could be used.

The inlet valve 4 is an active valve which can be closed or opened by a solenoid 5 under the control of the control circuitry. Instead of the active inlet valve 4 according to FIG. 1, a conventional check valve could also be employed. An inlet capillary 6 connects the output of the inlet valve 4 to the input of the pumping system. The pumping system comprises two substantially identical pump units which are connected in series, each unit being designed as a piston pump. The first pump unit comprises a pump chamber 7 having a cylindrical inner bore 8 for receiving a piston and a corresponding sapphire piston 10 for reciprocating movement inside the cylindrical bore 8. The pump chamber 7 has an inlet bore 9 at its lower end through which liquid supplied through the capillary 6 can flow into the cylindrical bore of the first pump chamber. The inlet bore 9 is located such that it is closer to the bottom dead centre than to the top dead centre of the piston 10. The outer diameter of the piston 10 is smaller than the inner diameter of the bore 8 of the pump chamber so that liquid can flow in the gap between the piston 10 and the inner surface of the bore 8. A seal 11 is provided at the bottom of the pump chamber 7 for sealing off the chamber at the opening through which the piston moves into the chamber so that no liquid can reach the outside. The driving mechanism of the piston will be described below in more detail.

The pump chamber 7 has an outlet bore at its top through which liquid can leave the first pump unit. The outlet bore is connected via a capillary 12 to an outlet valve 13 which can be, for example, a conventional check valve. The valve 13 permits liquid to flow only in a direction away from the first pump unit and inhibits flow of liquid in the opposite direction. A capillary 14 connects the valve 13 to the inlet of the second pump unit. The second pump unit comprises a pump chamber 18 having a cylindrical bore 19 for receiving a piston, a lateral inlet bore at the same relative location as the inlet bore of the first pump chamber, an outlet bore at the top of the chamber and a sapphire piston 20 for reciprocating movement inside the bore 19 of the chamber 18. The chamber 18 is sealed off by a seal 21 to avoid that any liquid leaves the chamber through the opening through which the piston extends into bore 19. The aforementioned components of the second pump unit thus have the same design as the corresponding components of the first pump unit.

The outlet of the second pump unit is connected via a capillary 22 to a damping unit 23 which serves for damping any pressure and flow variations which might occur in the outflow of the second pump unit. According to a preferred embodiment, a high pressure damper of the type is used which is known from DE-PS 33 06 631. This damper comprises two chambers separated by an elastic partition, with the first chamber receiving the fluid to be damped and the second chamber containing a compressible liquid such as water and a solid ceramic block which compensates for the different coefficients of expansion of the compressible medium and the housing of the second chamber. An integral component of the damping unit 23 is a sensor for measuring the pressure of the delivered liquid.

The output of the damping unit 23 is connected via a capillary 24 to the subsequent chromatographic system (separation column etc.) where the separation of the substances to be analyzed takes place.

It is understood that in an alternative embodiment of the invention, the damping unit can be arranged between the two pump units such that the input port of the damping unit is connected to the outlet valve 13 and that its output port is connected to the inlet of the second pump unit. All the other components of the pumping apparatus as well as the operation of the apparatus would be the same as in the embodiment shown in FIG. 1.

The sapphire pistons 10, 20 of the two pump units are driven by using a ball-screw drive for each piston. The lower ends of the piston 10, 20 are attached to piston holders 25, 26, respectively, and the piston holders are coupled via balls 27, 28 and actuators 37, 48 to recirculating ball spindles 30, 31, respectively. Also provided are return springs 15 and 29.

Figure 1A:
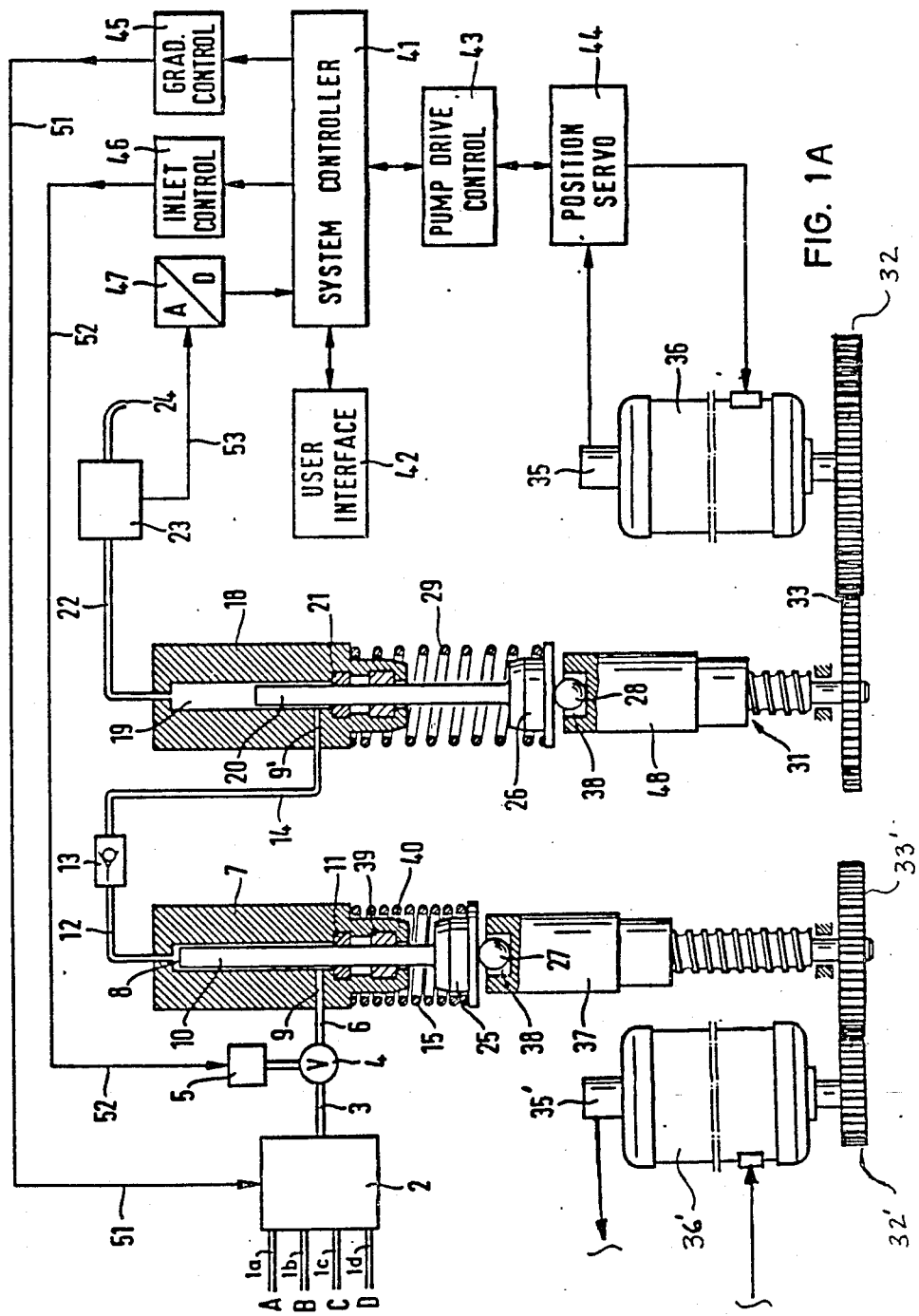

The ball-screw drives 30, 31 are coupled to toothed gears 33 and 34, respectively. The gears 33 and 34 are mating and gear 33 is coupled to a third gear 32 which is fixed to the shaft of a drive motor 36. According to a preferred embodiment, the proportions of the toothed gears 33 and 34 are selected such that gear 34 performs two revolutions when gear 33 performs one revolution. A digital indicator 35 for the angular position of the motor 36 is provided which permits to precisely determine the position of the pistons from the transmission ratios of the gears and the ball-screw drives. Alternatively, as shown in FIG. 1A, a separate motor 36' may be coupled via gears 32' and 33' to piston 10, allowing an adjustment of the relative phase of the reciprocating motions of the first piston 10 and the second piston 20.

Figure 2:
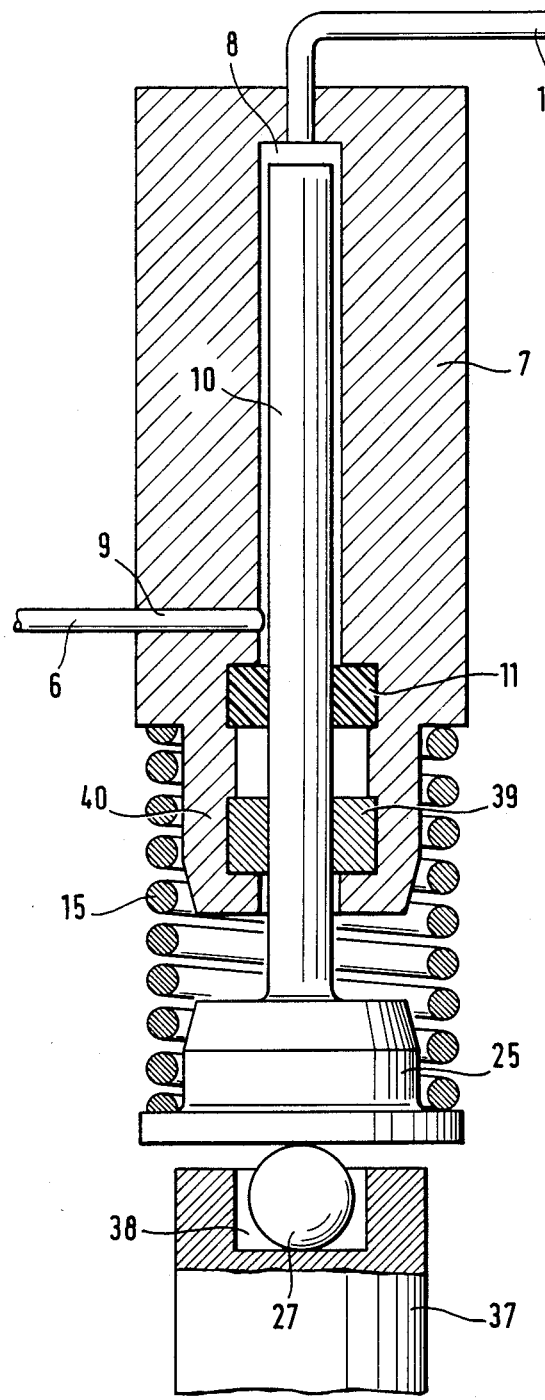
FIG. 2 is a detailed view of the coupling between the piston and the drive mechanism of the pumping apparatus according to FIG. 1.

Details of the coupling between the piston holders and the ball-screw drives are now explained with reference to FIG. 2 which is a detailed view of a part of the first pump unit of the pumping apparatus shown in FIG. 1. An actuator 37 which is rigidly connected to the ball-screw drive 30 comprises a recess 38 for receiving a ball 27. The ball 27 is free to move in the recess 38. The top of the ball 27 contacts the piston holder 25 connected to the piston 10. The piston is guided by a guiding element 39. The guiding element 39 is mounted to a mounting element 40 which is connected to the pump chamber 7. A return spring 15 is connected with one of the its ends to the pump chamber and with its other end to the piston holder 25. The return spring 15 pulls the piston downwards when the actuator 37 moves downwards. When the actuator moves upwards, the ball pushes against the piston holder so that the piston 10 moves upwards. The driving of the piston via the freely moving ball 27 in combination with the guiding element 39 ensures that the movement of the piston is free of tilt, resulting in an increased lifetime of the seal 11.

In the following, the control circuitry of the pumping apparatus of the invention is described with reference to FIG. 1.

A system controller 41 controls the function of the pumping apparatus in response to inputs made by a user via a user interface 42 coupled to the system controller. The user interface 42 can be any known input device, e.g., a keyboard. The user may input via the user interface 42, for example, a desired flow rate or a desired solvent mixture or a desired solvent gradient.

A pump drive controller 43 is connected to the system controller 41. A control loop for controlling the movement of the motor 36 is indicated by block 44. The actual value for the position of the motor 36 to be used in the control loop 44 is provided from the angular position indicator 35 and the nominal value is provided from the pump drive controller 43.

Also connected to the system controller 41 is a gradient controller 45 which supplies control signals via line 51 to the mixing valve 2 dependent on a desired solvent gradient selected by a user via user interface 42. The control signals permit a switching of the mixing valve 2 such that liquid can flow from one of the solvent containers A,B,C, or D through the valve to the first pump unit. By selection of the time intervals during which such a connection to a specific solvent container is established, a desired solvent gradient can be produced.

An inlet controller 46 coupled to the system controller 41 controls the opening and the closing of the inlet valve 4 in coordination with the movement of the piston 10. The control signals are supplied to the solenoid 5 on a line 52.

The pressure of the delivered liquid is measured by a pressure transducer arranged in the damping unit 23. The analog output signal of the pressure transducer is supplied on a line 53 to an A/D-converter 47 by which it is converted into a digital signal. This digital signal is supplied to the system controller 41 from which it can be passed to the user interface 42 and displayed.

Subsequently, the operation of the pump is described in two modes of operation, respectively, namely in the isocratic mode and in the gradient mode.

ISOCRATIC OPERATION

In the isocratic mode, one of the solvent containers A,B,C, or D is permanently connected to the inlet valve 4 so that always the same solvent is delivered. This can be accomplished either by holding the switching state of the mixing valve 2 fixed at one position so that its output is permanently connected to the same solvent container, or, alternatively, by operating the solvent delivery system without a mixing valve, so that one of the containers A,B,C, or D is directly connected to the input valve 4 without an intermediate mixing valve.

Upon start-up of the solvent delivery system, first of all, the top dead centre of the movement of the first piston 10 is determined. Under the control of the control circuitry, the first piston 10 slowly moves upwards into the bore 8 of the piston chamber until the piston holder 25 abuts the lower end of the pump chamber 7. Once this end position has been reached, the piston 10 moves back a predetermined path length. This position of the piston is defined as the top dead centre and the corresponding angular setting of the motor 36 determined by the indicator 35 is stored as a digital value in the control circuitry. Thus, the top dead centre can always be accurately reproduced by providing the motor control loop 44 with this digital value as a nominal value.

After this start-up procedure, the pump starts with its normal operation. The inlet valve 4 is opened by the solenoid 5 under the control of the inlet controller 46 and the piston 10 moves down from the top dead centre, thereby sucking solvent into the first pump chamber. According to the present mode of operation, the stroke length, i.e., the distance the piston travels between its top dead centre and its bottom dead centre is dependent on the flow rate which a user has selected at the user interface 42. From the information about the desired flow rate passed from the user interface 42 to the system controller 41, the system controller 41 computes the corresponding stroke length using a predetermined mathematical relationship between flowrate and stroke length (or stroke volume, which is proportional to the stroke length). An example of such a predetermined relationship between flowrate and stroke volume is explained below with reference to FIG. 4. Although, in the present mode of operation, there is a predetermined relationship between the flow rate and the stroke volume, the control circuitry of the present invention yet permits to put the coupling between flow rate and stroke volume out of action so that a free selection of the stroke length or volume becomes possible.

Once the first piston 10 has travelled the stroke length determined by the control circuitry from the top dead centre to the bottom dead centre, the drive motor 36 is stopped and the inlet valve 4 is closed so that no more liquid can flow into the first pump unit. Then, the motor 36 is restarted, now moving in the opposite direction as before until it again reaches the top dead centre. Then, the sequence starts anew with the piston moving down from the top dead centre to the bottom dead centre. Since the two pistons 10 and 20 are rigidly coupled to each other via gears 33 and 34, the second piston 20 operates with a fixed phase difference relative to the first piston 10. This phase difference is 180 degrees. As a consequence of the 180 degrees phase shift, the second piston 20 delivers liquid when the first piston 10 sucks in liquid and vice versa.

Since the gears 33 and 34 have a ratio of their circumferences of 2:1 and the ball-screw drives 31 and 30 are identical, the first piston 10 moves twice the path of the second piston 20 at any angular step of the motor 36. As a consequence thereof, the stroke volume V1 of the first pump unit is twice as large as the stroke volume V2 of the second pump unit, i.e., $V1=2*V2$. During the expulsion stroke of the first piston, the second piston sucks in half of the volume displaced by the first piston and during the suction stroke of the first piston, the second piston delivers the volume sucked in in the preceding half-cycle. Thus during a complete pump cycle (suction stroke and expulsion stroke) the volume V1 is delivered to the output of the pumping apparatus. In the embodiment of FIG. 1, the output of the second pump unit is connected to the damping unit 23 which serves for compensating for the delay in delivery at the beginning of the delivery phase of the first piston.

Figure 3:
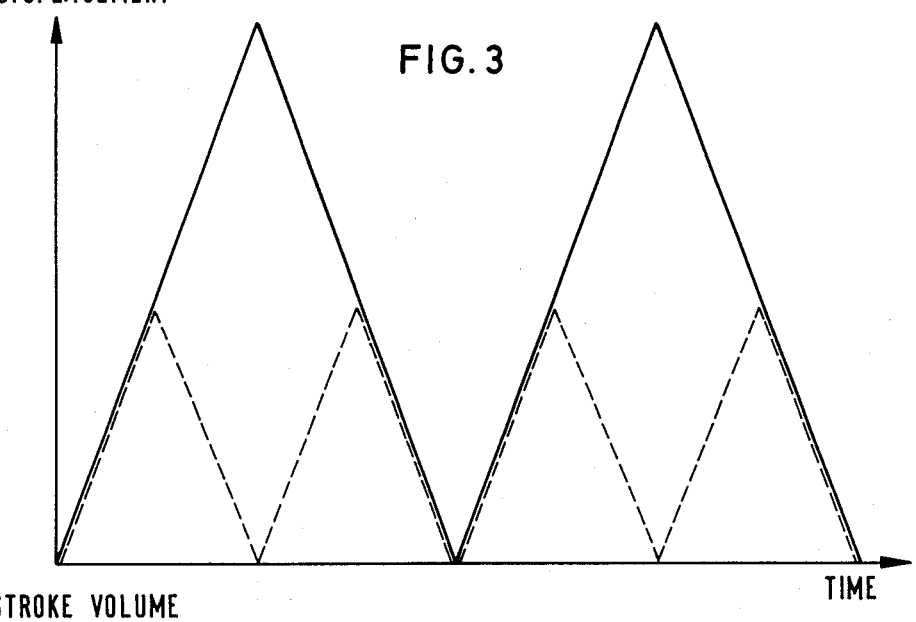
FIG. 3 is a graphical representation of the path travelled by the first piston in a pumping apparatus according to the invention plotted against time for two different stroke volumes.

The operation of the pump according to the invention is now further explained with reference to the diagrams in FIGS. 3 to 7. FIG. 3 shows a displacement-time diagram for the movement of the first piston 10, assuming a specified fixed flow rate. The horizontal axis is the time axis and the vertical axis is the axis for the displacement of the piston. The displacement-time diagram of FIG. 3 illustrates the preferred embodiment of the present invention that the paths travelled by the pistons are linear functions of time with two exemplary cases: in the first case, represented by the solid lines, the stroke length or stroke volume is twice as large as the stroke length or stroke volume in the second case, illustrated by the dashed lines. In both cases, the same amount of liquid is delivered within a specified time interval so that the resulting flow rates are identical. As can be seen from FIG. 3, the paths travelled by the pistons during the intake stroke or during the outtake stroke are linear functions of time, respectively, starting from the top dead centre (displacement=0), running to the bottom dead centre (maximum displacement), then returning to the top dead centre, and then repeating this sequence. The dashed curve has twice the frequency of the solid curve because the stroke path or stroke volume corresponding to the dashed curve is only half the stroke volume corresponding to the solid curve and the resulting flow rate is the same in both cases.

Figure 4:
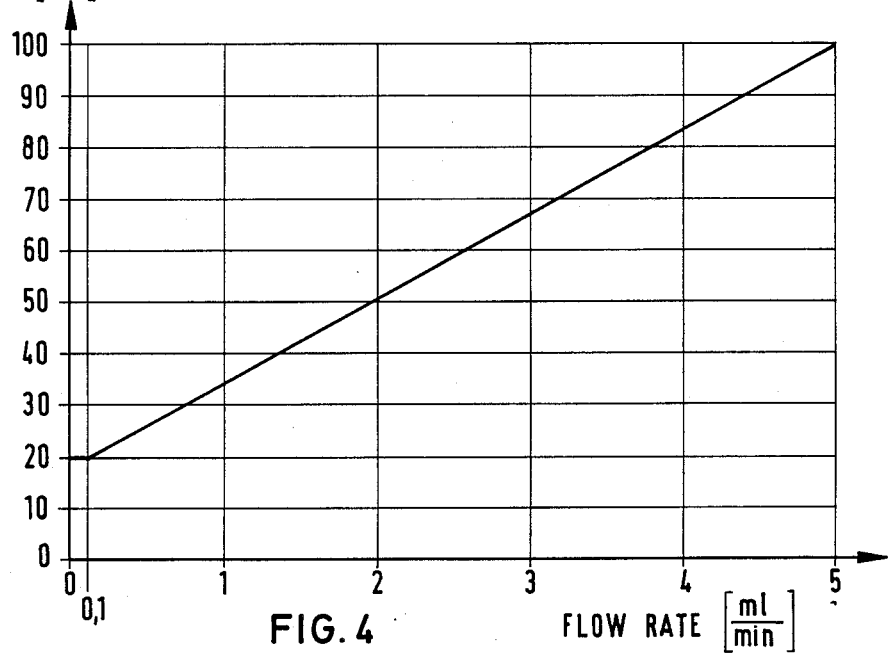
FIG. 4 is a graphical representation of the stroke volume displaced by the first piston in a pump according to the invention plotted against flow rate.

FIG. 4 shows an example how the stroke volume for the first piston 10 is varied with the flow rate of the delivered liquid. The relationship shown can be stored, for example, in the form of digital values in the system controller 41. It can be seen from FIG. 4 that, except for a small range of flow rates near zero, the stroke volume for the first piston is increased linearly with the flow rate, that means the plot of stroke length versus flow rate is a straight line. At very small flow rates below about 0,1 ml/min, the stroke volume is kept at a constant value down to zero flow rate. It is understood that the relationship plotted in FIG. 4 is not the only one possible but that various modifications thereto are possible, whereby it is preferred that the stroke volume is decreased when the flow rate is decreased.

Figure 5:
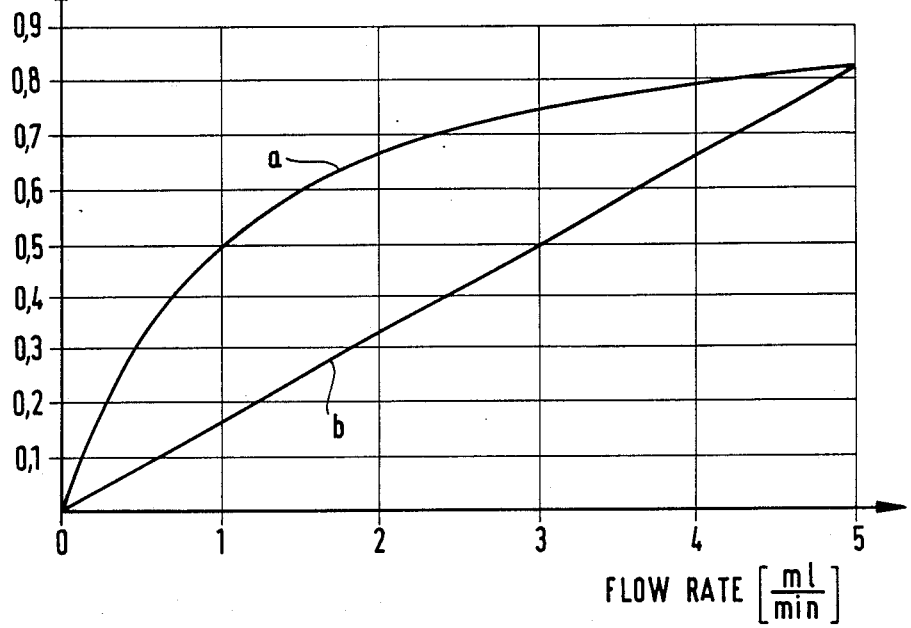
FIG. 5 is a graphical representation of the frequency of reciprocation of the pistons in a pumping apparatus according to the invention and in a conventional pump having a constant stroke volume.

In FIG. 5, the curve labelled "a" depicts the variation of the frequency of reciprocation of the pistons (pump frequency) with the flow rate assuming that the stroke volume is changed with the flow rate according to the function shown in FIG. 4. The pump frequency for each selected flow rate is determined by the system controller 41. The curve labelled "b" depicts the variation of the pump frequency with the flow rate for a prior art pumping apparatus having a fixed stroke volume of 100 microliters. Since, according to the invention, the stroke volume is changed with the flow rate, the pump frequency is a more complicated function of the flow rate than the straight line "b" of the prior art wherein the flow rate is increased by linearly increasing the pump frequency. The example according to FIG. 5 shows that for flow rates below 5 milliliters per minute, the pump frequency in a pumping apparatus according to the invention is larger than in the prior art pump. Since the pump frequency is larger, an remaining pulsations in the outflow of the pumping apparatus also occur with a higher frequency so that the ripple in the output signal of a detector coupled to the separation column has higher frequency than in prior art devices. Such an increase of the ripple frequency is advantageous with regard to accuracy and reproducibility of the chromatographic measuring results.

Figure 6:
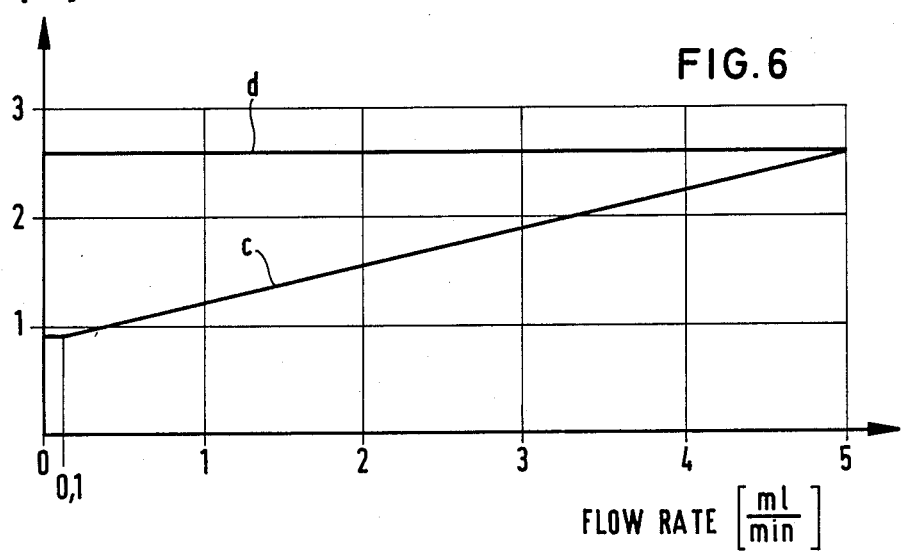
FIG. 6 is a graphical representation of the percent pulsation of the output flow in a pumping apparatus according to the invention and in a conventional pump having a constant stroke volume.

FIG. 6 illustrates the effect of a variable stroke volume on the pump pulsations. The horizontal axis of the diagram is the flow rate and the vertical axis of the diagram is the pump pulsation P in percent. The percent pump pulsation P is defined as $P = 100 * (p_{max} - p_{min})/p_{mean}$ wherein $p_{max}$ is the pressure in the delivered liquid when the second piston is directly before its top dead centre, $p_{min}$ is the pressure at the beginning of the compression phase of the first piston, and $p_{mean}$ is the mean pressure during a pump cycle. The pump pulsation is defined in terms of pressure, but with the assumption of laminar flow of the liquid, this is equivalent to a definition in terms of flow rate. In FIG. 6, curve "c" depicts the percent pulsation for a pumping apparatus according to the invention incorporating a relationship between flow rate and stroke volume as shown in FIG. 4, and curve "d" depicts the percent pulsation for a prior art pump having a constant stroke volume of 100 microliters. It can be seen that the invention leads to a substantial reduction of the percent pump pulsation.

GRADIENT OPERATION

In the following, gradient operation of the pump according to the invention is explained. For gradient operation, a mixing valve 2 connected to different solvent containers A,B,C, and D is required. For generating a solvent gradient, the mixing valve 2 is controlled during the intake stroke of the first piston 10 such that a specified solvent container is connected to the pump input for a certain fraction of the whole stroke path of the first piston. This fraction is calculated in the system controller 41 from the desired mixing ratio of the different solvents. The following example is to illustrate this situation:

If the user desires a mixing ratio of the four solvents in the containers A,B,C,D of 20:40:30:10, the system controller 41 computes, taking into account the stroke length for the present flow rate, the positions of the first piston at which a connection to the respective solvent containers has to be established through the mixing valve. At a flow rate of 5 ml/min, for example, the aspirated volumes of the solvents A,B,C,D, respectively, would be 20 $\mu$l, 40 $\mu$l, 30 $\mu$l, 10 $\mu$l, respectively, during one pump cycle, because the total volume aspirated by the first pump unit during a pump cycle, i.e., the stroke volume, has to be 100 $\mu$l according to the relationship between flow rate and stroke volume shown in FIG. 4. At a flow rate of 0,1 ml/min, the same solvent composition is achieved for the aspirated volumes 4 $\mu$l, 8 $\mu$l, 6 $\mu$l, 2 $\mu$l of the solvents A,B,C,D, respectively, because the stroke volume at a flow rate of 0,1 ml/min is 20 $\mu$l (see FIG. 4).

In contrast to this latter example, a pump having a fixed stroke volume of 100 $\mu$l would, in order to produce the mixing ratio of 20:40:30:10 at a flow rate of 0,1 ml per minute, suck in during a pump cycle liquid packages of 20 $\mu$l, 40 $\mu$l, 30 $\mu$l, and 10 $\mu$l. Thus, the liquid packages sucked in by a pumping apparatus according to the invention are much smaller than with pumps having a fixed stroke volume, so that the invention permits a better mixing of the different solvents. Therefore, in particular at small flow rates, an additional mixing unit as it would have to be provided in a pump having the fixed stroke volume of 100 $\mu$l is not necessary in a pumping apparatus according to the invention.

Figure 7:
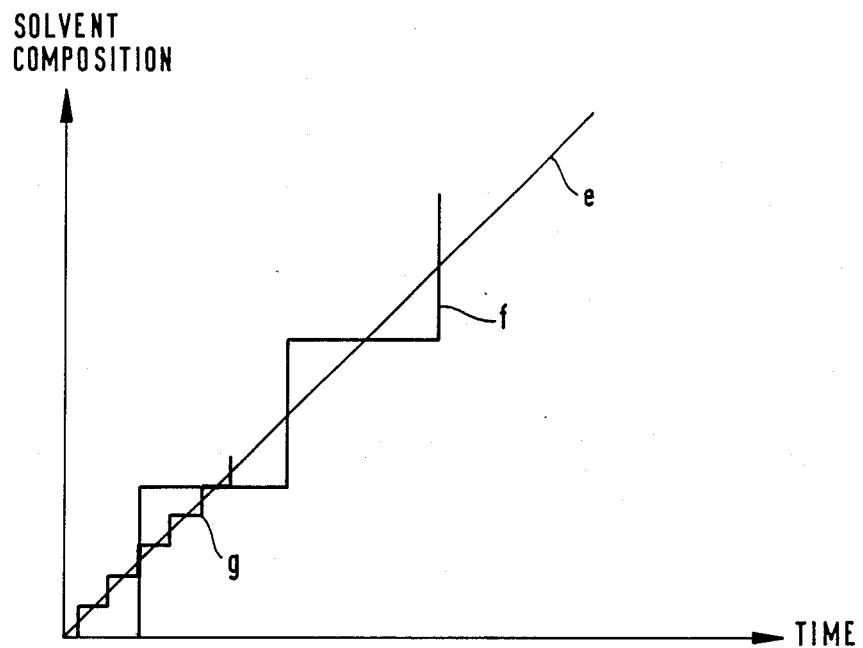
FIG. 7 is a graphical representation for gradient operation illustrating the change of the solvent composition as a function of time for a pumping apparatus in accordance with the invention and for a pump with a fixed stroke volume.

Reference is now made to FIG. 7 which is a graphical representation for gradient operation of a solvent delivery system. The horizontal axis is the time axis and the vertical axis is the axis for solvent composition, e.g., the concentration of a specific solvent within a mixture of various solvents. FIG. 7 shows three curves e,f, and g. Curve "e" illustrates the ideal course of a linear gradient, i.e. a straight line. Curve "f" is the course for state of the art solvent delivery systems having a constant stroke volume of, for example, 100 $\mu$l. It can be seen that the solvent composition is changed in comparatively coarse (large) steps. Curve "g" shows the course for a solvent delivery system according to the present invention. The steps are about five times smaller than in the state of the art. Further linearization of this step function is achieved through the system dead volume and an (optional) mixing unit which, however, is not required at flow rates smaller than about 4 ml/min.

With regard to gradient operation, the pump of the present invention has the further advantage that the packages of the different solvents leave the pump in the same order as they have entered the pump (first-in-first-out principle). This is due to the fact that the inlets of the two pump units, respectively, are located close to the bottom dead centres and the outlets close to the top dead centres of the pistons.

In the embodiment of the invention described above, the two pump units are driven by a common motor via toothed gears so that there is a fixed phase relationship of the movements of the two pistons. According to another embodiment of the invention, each of the two pistons can be driven by a separate motor which can be controlled independently from each other. With these two independent piston drives, the pump can be operated such that the solvent in the first pump unit is first compressed before the second pump unit has finished its delivery cycle. In that way, any remaining pulsation in the outflow of the pump due to solvent compressibility can be completely eliminated so that a pulse damping unit 23 is no longer required.

We claim:

1. Pumping apparatus for delivering liquid at a high pressure, comprising:
  a. a first piston (10) for reciprocation in a first pump chamber (7), the first pump chamber having an inlet port (9) and an outlet port,
  b. a second piston (20) for reciprocation in a second pump chamber (18), the second pump chamber having an inlet port (9') and an outlet port,
  c. a conduit connection (12,14) between the outlet port of the first pump chamber and the inlet port of the second pump chamber,
  d. an inlet valve (4) connected to the inlet port of the first pump chamber for allowing flow of liquid into the first pump chamber and for inhibiting flow in the opposite direction,
  e. an outlet valve (13) connected to the outlet of the first pump chamber for allowing flow of liquid into the second pump chamber and for inhibiting flow in the opposite direction,
  f. drive means (30,34; 31,33; 32,36) for reciprocating the first and the second piston, comprising ball-screw spindles (30,31) coupled to each of said pistons (10,20), respectively, and said drive means for each piston further comprising:
  an actuating element (37) having a recess (38) for receiving a ball (27),
  a ball (27) having such a diameter that it projects above the recess (38), but can freely move inside the recess,
  a piston holder (25) to which the piston (10) is mounted having a surface for contacting the ball (27),
  a return spring (15) for exerting a force on the piston (10) in a direction away from the pump chamber (7), and a guiding element (39) arranged between the actuating element (37) and the pump chamber (7) for guiding the piston (10), and
  g. control means (41,42,43,44,35) coupled to the drive means (30,34; 31,33; 32,36) for adjusting the stroke lengths of the pistons (10,20) between their top dead center and their bottom dead center, respectively, thereby permitting an adjustment of the amounts of liquid displaced by the first and second piston, respectively, during a pump cycle such that pulsations in the flow of the liquid delivered to the output of the pumping apparatus are reduced.

2. Pumping apparatus as in claim 1, wherein each ball-screw spindle (30,31) is coupled to a gear (34,33), with the gears of the spindles being coupled to each other and to a gear (32) coupled to the axis of a common drive motor (36) such that a rotary motion of the common drive motor causes a reciprocating movement of the two pistons (10,20) with a fixed phase relationship to each other.

3. Pumping apparatus as in claim 1 wherein each ball-screw spindle (30,31) is coupled to a separate drive motor allowing an adjustment of the relative phase of the reciprocating motions of the first piston (10) and of the second piston (20).

4. Pumping apparatus as in claim 1, wherein the two pistons (10,20) are reciprocating with a phase difference of 180 degrees and that the amount of liquid delivered by the first piston (10) during a pump cycle is two times as large as the amount of liquid delivered by the second piston (20) during that pump cycle.

5. Pumping apparatus as in claim 1, further comprising a damping element (23) connected either to the outlet of the first pump chamber (7) or to the outlet of the second pump chamber (18) for damping pulsations of the flow of the delivered liquid caused by the compressibility of the liquid said damping element comprising two chambers separated by an elastic partition, one chamber receiving the liquid to be damped, the other chamber holding a damping liquid, with an insert having a selected volume and temperature expansion coefficient being provided in the chamber holding the damping liquid.

6. Pumping apparatus as in claim 1, wherein, the inlet port (9) of the first and the inlet port (9') of the second pump chamber are located at that end of the chamber, respectively, from which the piston enters the chamber during its reciprocating motion, and the outlet port of the first and the outlet port of the second chamber are located at the opposite ends of the chambers, respectively.

7. Pumping apparatus as in claim 1, wherein said pump chambers have bores (8,19) whose inner diameters are larger than the diameters of the pistons (10,20), respectively, such that liquid can flow between the pistons and the inner walls of the bores of the pump chambers into the space above the pistons, respectively, so that liquid is drawn in when the pistons move in a direction out of the pump chambers, respectively.

8. Pumping apparatus as in claim 1, wherein said control means (41,43,44,35) controls the drive means in such a way that during the reciprocating movement of the pistons, the distances which the pistons travel from their top dead center to their bottom dead center and from their bottom dead center back to their top dead center, respectively, increase linearly with time.

9. Pumping apparatus as in claim 1, wherein said control means (41,43,44,35) controls the drive means such that the stroke lengths of the pistons (10,20) is decreased when the flow rate of the delivered liquid is decreased.

10. Pumping apparatus as in claim 1, wherein adjusting the stroke length of the first piston (10) is performed by either fixing the motion of the top dead center of the piston and the varying bottom dead center or the bottom dead center is kept fixed and the top dead center is varied.

11. Pumping apparatus as in claim 1, wherein a mixing valve (2) coupled with its output to the inlet valve (4) of the first pump chamber (7), the mixing valve having a plurality of inputs (1a,1b,1c,1d), each coupled to different containers (A,B,C,D) containing different solvents, the mixing valve being responsive to control signals from a gradient controller (45) connected to the control means for establishing connections to a selected solvent container during adjustable portions of the inlet stroke of the first piston (10), so that a desired mixture of solvents can be generated.

12. Pumping apparatus as in claim 11, wherein said apparatus is used for generating solvent gradients.

* * * * *